(12) United States Patent
Albientz et al.

(10) Patent No.: US 8,329,872 B2
(45) Date of Patent: Dec. 11, 2012

(54) DRUG MONITORING ASSAY

(75) Inventors: Patrick Albientz, St. Louis Neuweg (FR); Jean-Michel Grenet, Village Neuf (FR); Rainer Hillenbrand, Shanghai (CN); Francois Legay, Saint Louis (FR); Peter Marbach, Therwil (CH); Severine Marrony, Eschentzwiller (FR); Judith Schaefer, Liestal/BL (CH)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 13/290,581

(22) Filed: Nov. 7, 2011

(65) Prior Publication Data

US 2012/0115247 A1    May 10, 2012

Related U.S. Application Data

(63) Continuation of application No. 12/678,840, filed as application No. PCT/EP2008/062891 on Sep. 26, 2008, now Pat. No. 8,076,160.

(30) Foreign Application Priority Data

Sep. 27, 2007    (EP) .................................... 07117444

(51) Int. Cl.
  *G01N 33/53* (2006.01)
  *G01N 33/577* (2006.01)
  *C07D 403/14* (2006.01)
(52) U.S. Cl. ............... 530/387.1; 435/189; 435/196; 435/207; 435/192; 436/501; 530/388.9; 530/389.8; 530/363; 544/284
(58) Field of Classification Search .................... None
See application file for complete search history.

(56) References Cited

U.S. PATENT DOCUMENTS

| 6,645,970 B2 | 11/2003 | Albert et al. |
| 2006/0141548 A1 | 6/2006 | Roberts et al. |

FOREIGN PATENT DOCUMENTS

| WO | WO 02/38561 | 5/2002 |
| WO | WO 2003/089928 | 10/2003 |
| WO | WO 2005/088307 | 9/2005 |

OTHER PUBLICATIONS

International Preliminary Report on Patentability issued for PCT/EP2008/062891 on Mar. 30, 2010.*
Skvara H et al. "A 2 week multiple ascending dose, double-blind placebo controlled study to evaluate the safety, tolerability, pharmacokinetics and efficacy of oral AEB071, a protein kinase C inhibitor, in moderate to severe psoriasis patients", Journal of Investigative Dermatology, vol. 127, No. Suppl. 1, p. S43, (2007).
Alak A M. "Measurement of Tacrolimus (FK506) and its Metabolites: A Review of Assay Development and Application in Therapeutic Drug Monitoring and Pharmacokinetic Studies", Therapeutic Drug Monitoring, vol. 19, No. 3, pp. 338-351, (1997).
Ibrahim et al., Non-HLDA8 animal homologue section anti-leukocyte mAbs tested for reactivity with equine leukocytes:, Veterinary Immunology and Immunopathology, vol. 119, No. 1-2, pp. 81-91, (2007).
Wrenshall et al., "Influence of interleukin-2 deficiency on the generation of autoimmune B cells", Journal of Autoimmunity, vol. 29, No. 2-3, pp. 125-133, (2007).
Choi et al., The DE loop of the domain III of the envelope protein appears to be associated with West Nile virus neutralization, Virus Research, vol. 123, No. 2, pp. 216-218, (2007).

* cited by examiner

*Primary Examiner* — Shafiqul Haq
*Assistant Examiner* — Galina Yakovleva
(74) *Attorney, Agent, or Firm* — Jennifer C Chapman

(57) ABSTRACT

A method for obtaining at least one binding agent which binds a pharmaceutically active form of the compound with a higher specificity than a pharmaceutically inactive form of the compound is described by using special derivatives of said parent compound. The invention also pertains to the respectively created binding agents and derivatives. Furthermore, drug monitoring assays using said binding agents for monitoring pharmaceutically active forms of said parent compound are provided.

1 Claim, 2 Drawing Sheets o Curve A
□ Curve B

DRUG MONITORING ASSAY

This application is a continuation of application Ser. No. 12/678,840 filed Mar. 10, 2010 now U.S. Pat. No. 8,076,160, which is a 371 of PCT/EP08/062891 filed on Sep. 26, 2008, which claims benefit of EP Application No. 07117444.5, filed Sep. 27, 2007, which in their entirety are herein incorporated by reference.

Qualitative and quantitative assays are of great importance in different fields of life sciences. The present invention relates generally to reagents and methods for the determination of drug compounds in biological fluids. In particular, a biological assay is provided for determining the amount or concentration of an active ingredient such as e.g. a pharmaceutical compound present in a sample. Furthermore, methods are provided for obtaining binding agents that recognize the pharmaceutically active metabolites of a compound. Respective binding agents are valuable tools in drug monitoring assays.

In pharmacology, many medications are used without monitoring of blood levels or other body fluids, as their dosage can generally be varied according to the clinical response that a patient gets to that substance. With some drugs this approach is, however, impossible or at least difficult, as insufficient levels of drug will lead to undertreatment or resistance, and excessive levels can be toxic and/or tissue damaging. Therapeutic drug monitoring is a branch of chemical chemistry that specializes in the measurement of medication levels in blood or other biological samples. Its main focus is on drugs with a narrow therapeutic index, i.e. drugs that can easily be under- or overdosed. In order to provide an optimized therapeutic treatment, it is therefore beneficial to monitor respective drugs. Examples of respective drugs which usually need drug monitoring are anti-infective agents such as gentamicin and vancomycin; aminoglycoside antibiotics; immunosuppressants such as ciclosporin, everolismus; antiepileptic drugs; antipsychotic such as clozapine and lithium, anticancer drugs, digoxin and others.

In order to achieve a therapeutic effect, particularly drugs acting as enzyme inhibitors should be administered in dosages that provide sufficient inhibition of the enzyme involved. However, as the patient's metabolism varies, also the dosage requirements can vary strongly between the patients. AEB071 is a selective and potent inhibitor of classical and novel protein kinase C (PKC) isoforms with $k_i$ values in the nM range.

Prodrugs are pharmaceutical compounds which are administered in a form having less or even no pharmaceutical activity. Once administered, the prodrug is metabolised in vivo into the active compound. The rationale behind the use of a prodrug is generally for absorption, distribution, metabolism, and excretion (ADME) optimization. Regarding prodrugs it is often necessary to monitor that sufficient amounts of the prodrug are converted to the pharmaceutically active metabolite in order to obtain the therapeutic effect.

The term "parent drug" in the context of drug monitoring usually denotes the molecular structure of a drug at the time it is administered to the patient. Once absorbed, the parent drugs may be subjected to chemical changes called biotransformation (metabolism), which results in altered molecules called metabolites. The gut wall and liver harbor the greatest concentration of metabolizing enzymes, which are often described as microsomal enzymes because they are concentrated in vesicles within the endoplasmatic reticulum of cells. However, enzymes are ubiquitous and catalyze biotransformation at countless additional sites.

Both parent drugs and their metabolites can have varied degrees of pharmacological activity, designated active or inactive, and can also vary in their potential for toxicity. For example, a sedative that is active as a parent drug might be converted to three inactive metabolites but also to one that is active and sedative, but another that is active and cardiotoxic. Furthermore, each of these molecular forms can exhibit varied patterns of distribution and elimination. These metabolic changes make the detection of the pharmaceutically active concentration of the drug compound difficult as inactive metabolites if they are recognized in the monitoring assay may lead to false results.

Particularly designing a monitoring/immunoassay for the detection of a small molecule can be a challenge. Such small molecules often lack antigenicity, making it difficult to generate e.g. antibodies that bind the small molecule. To increase the immunogenicity of small molecules, larger antigenic compounds, such as proteins or polypeptides can be conjugated to the drug.

In order to monitor pharmaceutical compounds, diagnostic tools have been developed to monitor the therapeutic effect of drugs in a patient at a certain concentration. Most of the known drug monitoring methods make use of antibodies which bind the pharmaceutical compound that is supposed to detect/monitor in a patient sample. However, an efficient monitoring is very difficult, as a proper differentiation between the active forms of the drug and e.g. inactive metabolites is important in order to determine the therapeutically active concentration of the compound. The problems that are associated with a respective cross-reactivity to inactive metabolites are well known in the prior art (see for example Rentsch et al, 2006: Therapeutic drug monitoring der Immunsuppressiva).

SUMMARY OF THE DISCLOSURE

It is the object of the present invention, to provide drug monitoring assays which have a low probability of detecting inactive metabolites of a drug compound. It is also the object of the present invention to provide methods for developing respective specific drug monitoring assays, in particular for producing appropriate binding agents such as antibodies specifically recognizing the active forms of the compound to be monitored. It is a further the object of the present invention to identify and provide appropriate binding agents that have a higher probability of specifically binding pharmaceutically active forms of the compound AEB071. Respective binding agents may be used in a drug monitoring assay for AEB071.

DETAILED DESCRIPTION OF THE DISCLOSURE

Figure 1:
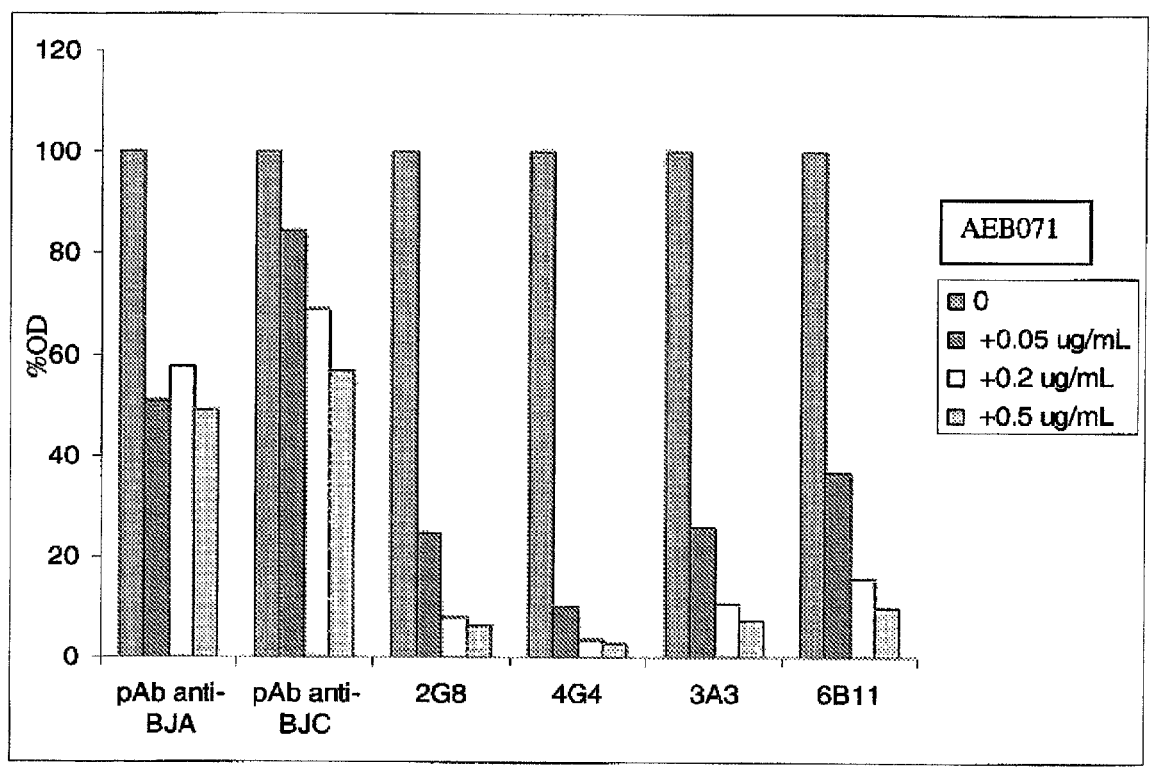
FIG. 1: Specificity test for monoclonal and polyclonal anti-AEB071 antibodies.

According to a first embodiment of the present invention a method is provided for obtaining at least one binding agent, which binds at least one pharmaceutically active form of a parent compound with a higher specificity than a pharmaceutically inactive form of said parent compound, comprising (a) preparing at least one derivative of said pharmaceutically active form of said parent compound by shielding a part of said pharmaceutically active form of said parent compound;

(b) using said derivative for obtaining a group of binding agents that bind said derivative;

(c) selecting at least one binding agent from said group of binding agents that binds the derivative as well as at least one pharmaceutically active form of said parent compound.

One aspect of the present invention pertains to providing at least one binding agent, which specifically binds the pharmaceutically active form of a pharmaceutical compound and which has a lower probability of binding inactive metabolites.

In order to obtain respective specific binding agents, the present invention uses a defined method for obtaining/raising respective binding agents. According to one important aspect, not the parent compound is used for obtaining said binding agent, but a specifically designed derivative thereof.

The derivatives are designed based on the structure of the parent compound such that they have the highest probability to generate binding agents which would recognize a pharmaceutically active form of the parent compound but which have the least probability to recognize pharmaceutically inactive metabolites of the parent compound. To achieve that result, certain parts of the compounds are shielded from binding of a binding agent. By using a respective shielding structure, binding agents have no access to the shielded regions of the molecule. This has the effect that binding agents can be obtained that are directed to the unshielded and thus accessible parts of the molecule. In one embodiment of the invention, the unshielded part(s) of the molecule correspond to those sites of the molecule, where metabolic actions can inactivate the compound. Thereby, binding agents can be obtained, that recognize the chemical structure corresponding to the active chemical structure of the molecule. Hence, if metabolic changes alter/change that the part of the molecule that is recognized by the binding agent, binding of the binding agent may be at least decreased or completely prevented. This measure ensures that the binding agents are more specific to the active chemical structure at the site recognized by the binding agent.

In order to confirm that the intended site of the molecule is at least partially recognized by the binding agent one may design a derivative comprising a shielding structure shielding the metabolic site of interest. A respective derivative may be used to analyze whether the binding agent has a high specificity for the intended site as a specific binding agent obtained by the method of the present invention should not bind or would bind with a lower specificity said derivative wherein said metabolic site is shielded. Such a derivative may constitute a valuable tool for selecting very specific binding agents.

Afterwards, those binding agents are selected from the group of obtained binding agents, which bind the derivative as well as the pharmaceutically active form of the parent compound. This selection is important in order to eliminate binding agents that e.g. recognize the shielded structure and are thus not specific for the molecule. A respective selection can e.g. be performed by competitive assays, as described in further detail below. This method allows to optimize the generation of binding agents specific against certain compounds, in particular small compounds by using a standard procedure.

In case a binding agent is supposed to be produced that is specific for a defined active metabolite of the parent compound (as may be the case for prodrugs), the chemical structure of the parent compound may be altered when designing the derivative in order to closely resemble the chemical structure of the active metabolite to be detected. This ensures that the binding agent recognizes the correct chemical structure of the intended target, the active metabolite. This modified structure resembling the chemical structure of the active metabolite is not shielded in a respective derivative but exposed and thus accessible in order to ensure that binding agents are created that specifically recognize/bind this portion of the molecule that is chemically altered when converting the parent compound to the active metabolite in the body. The group of binding agents obtained with a respective derivative can be selected for binding agents that specifically recognize the chemical structure of the active metabolite but not that of the (inactive) parent compound As was outlined in the general introduction, a parent compound may have several different metabolites, some may be active, some inactive. According to one embodiment, the binding agents selected recognize more than one pharmaceutically active form of the parent compound, e.g. the parent compound and at least one further active metabolite thereof. However, for certain drugs or uses it may be important to differentiate between different pharmaceutically active forms of the parent compound and thus e.g. between the active parent compound and at least one further pharmaceutically active metabolite thereof. In this case, the binding agents are selected such, that they bind the desired target (either the parent compound or the active metabolite) with a higher specificity. This can be achieved e.g. via competitive binding assays using the parent compound and the active metabolite as competing targets. Thereby, those binding agents may be selected that depict the desired selectivity for the intended target.

For parent compounds which have more than one site where the compounds could be inactivated through metabolic actions, at least two derivatives may be created, wherein each derivative is shielded at a different site of the molecule from binding. Depending on the number of potential metabolic sites, the number of derivatives may be adjusted to the number of metabolic sites which may lead to inactivation of the molecule in order to obtain a binding agent which binds at least one pharmaceutically active form of a parent compound with a higher specificity than a pharmaceutically inactive form of said parent compound.

A "derivative" refers to a chemical compound or molecule that can be imagined to arise from a parent compound by replacement of one atom with another atom or group of atoms. Derivatives can e.g. be made based on the structure of the parent compound by one or more chemical reactions (e.g. the attachment of a linker). However, depending on the type of modification (e.g. in case the basic chemical structure of the parent compound is modified in order to resemble pharmaceutically active metabolites), a different synthesis pathway may be necessary. Derivatives according to the present invention comprise a modification, wherein a certain site of the parent compound is shielded, thereby usually preventing binding of respectively obtaining a binding agent recognizing the shielded portion of the molecule.

The term "pharmaceutically active form of a parent compound" refers to the parent compound as well as to pharmaceutically active metabolites. At least one of those needs to be recognized by the binding agent, e.g. the parent compound or an active metabolite thereof. To develop a binding agent that specifically recognizes an active metabolite may be particularly useful in case the activity of a prodrug is supposed to be monitored, as prodrugs are usually administered in an inactive (or significantly less active) form, which is then metabolized to the therapeutically active metabolite. A parent compound may also be inactivated at several different sites of the molecule. Hence, at least one pharmaceutically active form of a parent compound is recognized by the binding agent. This may be site specific, as the binding agent may only recognize one portion of the molecule (the epitope in case of the antibody). If the parent molecule is inactivated at a different metabolic site—not recognized/bound by the binding agent—this inactivation may not be recognized by a respective binding agent. In this case, several binding agents recognizing different parts of the molecule where inactivation may occur could be used in combination. This, however, depends on the parent compound and how it is metabolized and therefore needs to be evaluated based on the individual case.

"Pharmaceutically active" particularly refers to the intended therapeutic effect of the compound. However, this term also includes other important pharmacological activities, such as e.g. toxic effects. This, as in some cases monitoring of e.g. toxic metabolites in a patient is intended and therefore, specific binding agents can be useful that specifically recognize the toxic metabolites.

Shielding of the parent compound for obtaining the derivatives can be achieved by using a chemical shielding structure which is coupled to the molecule. This shielding structure may be a chemical group suitable for blocking those parts of the molecule that are supposed to be shielded. Such a blocking group may be any group which when bound to one or more hydroxyl, amino or carboxyl groups of the pharmaceutically active form of the parent compound (including intermediates thereof such as the aminolactams, aminolactones, etc.) prevents reactions from occurring at these groups. Particularly binding of a binding agent is supposed to be prevented at those shielded sites when said derivative is used for obtaining the binding agents. Usually, when respective shielding structures are present, binding agents would attack/recognize the shielding structure, but not the underlying chemical structure. A suitable shielding structure may comprise a carrier which is attached to the site of the molecule to be shielded.

Said coupling may be performed by using a linker structure. Suitable linkers may be selected from the group consisting of acylating groups which react with the amino groups of said carrier, alkylating groups which react with sulfhydryl (mercapto), thiomethyl, imidazo or amino groups on said carrier, most preferably maleimide groups, ester and amide forming groups which react e.g. with a carboxyl group of a protein, disulfide forming groups which react with the sulfhydryl groups on said peptide unit, such as 5,5'-dithiobis (2-nitrobenzoate) groups, ortho-pyridyl disulfides and alkylmercaptan groups, dicarbonyl groups, such as cyclohexandione groups, and other 1,2-diketone groups; diazo groups, which react with phenolic groups. The linkers may be elongated by appropriate alkyl groups, e.g. having 2 to 20 C-atoms, preferably 2-10 C-atoms. Particularly suitable linkers were used in the derivates A and B (see below) which may also be used for obtaining derivates of different parent compounds.

The parent compound may be a small molecule. As outlined in the introduction, obtaining binding agents for the detection of a small molecule is particularly challenging, as it is difficult to obtain binding agents against small molecules. For this reason it is beneficial to use a carrier when raising antibodies.

The parent compound may be selected from the group consisting of immunosuppressants, anti-infective agents, antiepileptic drugs, antipsychotics and anticancer drugs. These drugs are particularly difficult to dose and the effects resulting from a wrong dosage can be severe. This particularly applies to immunosuppressants used in transplantation. Therefore it is particular beneficial to monitor respective compounds. However, generally any pharmaceutically compound can be monitored/used for obtaining specific binding agents by the method of the present invention.

According to one embodiment, the parent compound is a small molecule. As outlined in the introduction, small molecules are difficult to monitor. However, the present invention allows to obtain specific binding agents for small molecules. According to one embodiment, the small molecule is a protein kinase C (PKC) inhibitor. According to one embodiment, which was also used in the described examples, the parent compound AEB071 is used as parent compound which is supposed to be monitored. This compound has the following chemical structure:

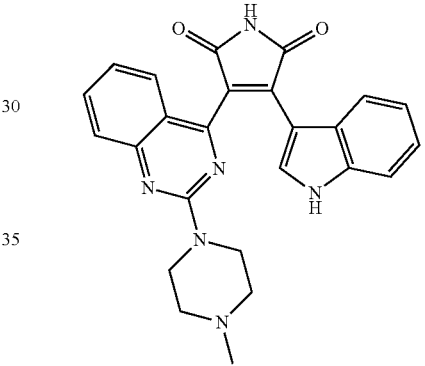

This compound (PKC inhibitor) is an immunosuppressant with an improved therapeutic window/profile.

For obtaining suitable binding agents allowing to monitor AEB071 in a sample, at least one derivative may be used, which has the following chemical structure:

A shielding structure such as a carrier may be attached e.g. to the position $X_1$ and/or $X_2$. In case no shielding structure is attached, $X_1$ and/or $X_2$ may be hydrogen. At least one of $X_1$ and $X_2$ comprises a respective shielding structure. Coupling may occur via a linker structure, as described above.

According to one embodiment, the derivatives A and/or B are used as derivatives for generating binding agents:

Derivative A

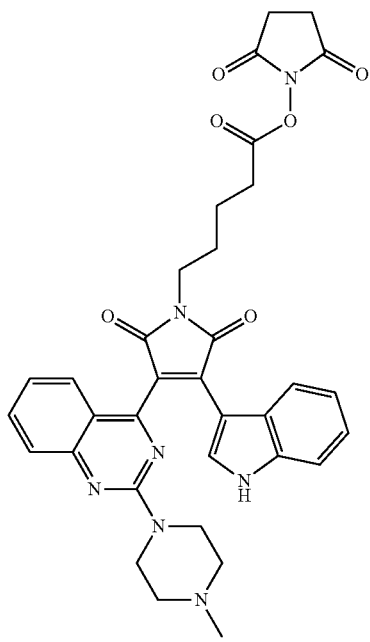

Derivative B

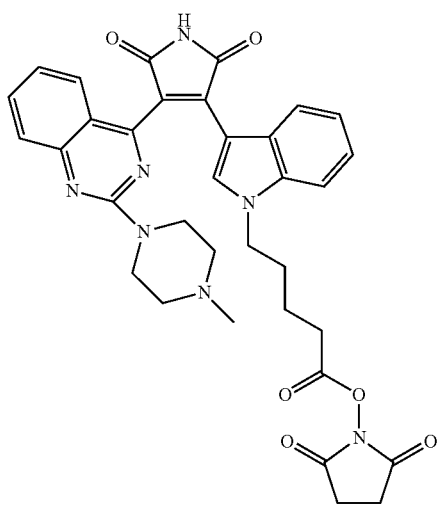

These derivatives are particularly useful for obtaining binding agents that are specific for the parent compound AEB071 when performing the method according to the present invention.

The selection step (c) according to the present method wherein those binding agents are selected, which have the highest probability of binding to pharmaceutically active forms of the parent compound, are preferably selected by analyzing whether the presence of the pharmaceutically active form of the parent compound inhibits binding of the binding agent to the derivative. A suitable method for performing a respective analysis is to perform a competitive binding assay using the derivative as binding partner which competes with the pharmaceutically active form of the parent compound as target for said binding agent. One embodiment for performing a respective competitive binding assay is an immunoassay such as an ELISA assay. However, also other immunoassay methods may be used for this analysis. Hence, according to one embodiment of the present method an immunoassay is performed for determining the binding specificity of the binding agents.

According to one embodiment which is particularly suitable in case the parent compound has more than one metabolic site where it could be inactivated by metabolic actions or the compound is larger thereby providing several epitopes for the binding agent, at least one binding agent is selected in step (c) which specifically binds to the pharmaceutically active form of the parent compound, the derivative against which it was obtained and which also bind to at least one different derivative of the parent compound, which shields a different part of the molecule than the first derivative, but which leaves the same part of the molecule exposed as the first derivative. By performing a comparative analysis of the binding patterns of the binding agent to the different derivatives it can be determined, which specific part of the pharmaceutically active form of the parent molecule is bound/recognized by the binding agent, as a different part of the parent molecule is shielded from binding in each derivative used. The binding region (i.e. epitope in case of an antibody) of the compound can be further determined or analyzed by creating a derivative wherein the intended/assumed metabolic site of the molecule is shielded. A binding agent specific for said shielded region would not bind a respective derivative. Therefore, such derivatives wherein the metabolic sites are shielded may be used to confirm the specificity of the obtained binding agents.

According to one embodiment, a binding agent is selected in step (c) which differentiates between the molecule AEB071 and an active metabolite thereof, which has the following structure:

Compound C:

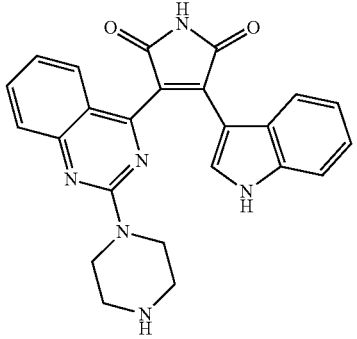

As can be seen, the methyl group at the piperazine ring which is present in AEB071 is missing in Compound C. As described herein, appropriate binding agents can be selected by performing a competitive assay between the parent compound AEB071 and the Compound C, as described herein.

Suitable binding agents may be obtained by screening a binding agent library in order to identify/obtain binding agents that bind the derivative(s) prepared according to the teachings of the present invention. Examples for respective binding agent libraries are for example phage or phagemid libraries, which display the binding agents. Methods for obtaining e.g. antibodies in vitro are also described in Hudson, P J and Souriau, C. (2003) Engineered antibodies. Nat. Med. 9, 129-134), herein incorporated by reference.

The binding agents may have any structure, as long as they are able to specifically recognize and bind a target. Binding agents may be selected from the group consisting of antibodies, antibody fragments or variants thereof having a binding function, binding agents having a protein scaffold providing a binding function such as for example anticalines. An overview of binding agents, which have a similar binding function as antibodies is given in Hey, et al: Artificial, non-antibody binding proteins for pharmaceutical and industrial application, Trends in Biotechnology, Vol 23 No. 10, October 2005 page 514-522, herein incorporated by reference. An antibody fragment is any fragment of an antibody comprising at least 20 amino acids from said whole antibody, preferably at least 100 amino acids which still has a binding capacity. In a preferred embodiment the antibody fragment comprises the binding region of the antibody such as a Fab fragment, a F(ab)2 fragment, multibodies comprising multiple binding domains such as diabodies, triabodies or tetrabodies, single domain antibodies or affibodies. An antibody variant is a derivative of an antibody or antibody fragment having the same binding function but e.g. an altered amino acid sequence.

According to one embodiment, the binding agent is an antibody. The use of antibodies has the advantage that they can be easily generated by e.g. administering said derivative described above to an animal to effect a specific immunogenic response to said derivative.

The animal may be selected from the group consisting of mouse, rat, rabbit, chicken, guinea pig, goat and sheep. The antibody may be a monoclonal or a polyclonal antibody. Suitable methods for obtaining respective antibodies are described in "Antibodies—A laboratory Manual" by Ed Harlow and David Lane, 1988 and/or "Monoclonal antibody protocols" by W. C. Davies, 1995, herein incorporated by reference. Due to the higher specificity of monoclonal antibodies, monoclonal antibodies are usually preferred. Monoclonal antibodies may be obtained by recovering at least one antibody producing cell from an animal which was immunized with the derivative, immortalizing said antibody producing cell and isolating a monoclonal antibody from the immortalized antibody producing cell.

Suitable carriers that may be used in the context of the present invention include proteins, glycoproteins, complex polysaccharides and particles. Various proteins may be employed as carrier. These proteins include but are not limited to albumins and serum proteins, for example globulins, ocular lens proteins, lipoproteins and the like. Illustrative proteins include bovine serum albumin (BSA), keyhole limpet hemocyanin (KLH), egg ovalbumin (ova), bovine gamma-globulin (BGG) and similar proteins. Also synthetic carriers may be used. Suitable polysaccharide are for example starches, glycogen, cellulose or carbohydrate gums may be used as carrier. The use of a carrier for shielding is particularly preferred if an animal is supposed to get immunized with a small molecule, as the carrier increases the immunogenicity of the compound.

With the method described above, suitable binding agents can be obtained which bind at least one pharmaceutically active form of a parent compound with a higher specificity than a pharmaceutically inactive form of said parent compound. One key element of the present invention lies in the design of the derivatives used which is described in detail above. Respective binding agents are therefore very suitable for use in high sensitive and reliable drug monitoring assays. The binding agents according to the present invention are designed/selected such, that they predominantly bind an active form of the parent compound. In some embodiments, they are designed such that they are even able to distinguish between different forms of active metabolites. This specificity is an important advantage, as it is prevented that inactive metabolites of the parent compound are accidentally detected which could falsify the obtained drug monitoring results.

Additionally, the present invention provides respectively designed derivatives and the obtained binding agents. The derivates can be obtained as described by modifying the parent compound such, that those parts of the parent molecule are shielded where no or no relevant metabolic action takes place which would inactivate the parent compound. This has the effect that the binding agents are raised to the relevant parts of the compound. Depending on the size of the parent compound, also several derivates may be created in order to successively shield all parts of the parent compound by creating different derivatives. The part where metabolic inactivation occurs usually remains unshielded. Binding agents binding specifically to the portion of the molecule that is accessible (unshielded) in all derivatives, can be selected by testing the cross-reactivity of said binding agent to said derivatives.

Particularly, the present invention provides a derivative of AEB071, having the following basic structure:

wherein $X_1$ and/or $X_2$ resemble the coupling site of a shielding structure or hydrogen. At least one site $X_1$ or $X_2$ carries a shielding structure. E.g. a carrier may be coupled as shielding structure to the chemical skeleton via a linker structure, as described above. It was found that shielding the parent molecule AEB071 at the sites $X_1$ and/or $X_2$ leads to derivatives, which allow the generation of binding agents, which are very specific for the parent compound and thus to the pharmaceutically active compound. Due to the defined shielding pattern of these derivatives, wherein the attachment points for a linker structure are carefully chosen to leave the potential metabolic sites accessible, these derivatives are valuable tools for generating binding agents specific for the parent compound.

Defined examples of respective derivatives are Derivative A and Derivative B:

Derivative A:

Derivative B:

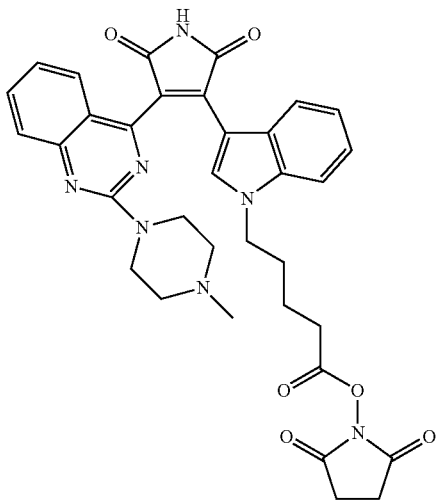

Also provided by the teaching of the present invention is a variant of AEB071, having the following structure:

Compound C:

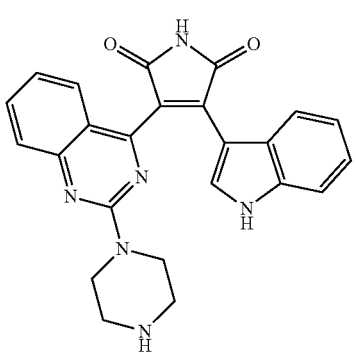

This variant can be used—as described above—in order to select antibodies which bind the parent compound AEB071 with a higher specificity than the active metabolite Compound C. For performing respective tests, this compound can be provided e.g. with a detectable label or carrier.

Also provided with the present invention is a binding agent which is obtained by the described screening method. According to one embodiment which is especially suitable for monitoring/detecting the parent compound AEB071, the binding agent is selected by using one of the above defined derivatives of AEB071—in particular Derivative A and/or Derivative B. According to one embodiment, the parent compound AEB071 is bound with a higher specificity than the Compound C by said binding agent. Preferably, said binding agent is an antibody selected from the group consisting of 2G8, 4G4, 3A3 or 6B11. Preferred antibodies according to the invention are 4G4, 3A3.

According to a further aspect of the present invention, a drug monitoring assay is provided, comprising:
- contacting a sample assumed of comprising at least one pharmaceutically active form of a parent compound with at least one binding agent;
- determining the concentration of said pharmaceutically active form of said parent compound by using at least one binding agent which binds the pharmaceutically active form of said parent compound with a higher specificity than a pharmaceutically inactive form of said compound.

Appropriate binding agents which can be used in a respective assay can be obtained by the method described above. The key elements of the method described in detail above are the in silico a priori design of suitable derivatives which generate binding agents recognizing the metabolically critical part(s) of the molecule where inactivation may occur, the selection of binding agents binding the derivatives and the pharmaceutically active form of the parent compound by using competitive experiments, thereby obtaining binding agents recognizing the pharmaceutically active form of the parent compound.

In the drug monitoring assay according to the present invention, a competitive assay may be performed for determining the concentration, using a target compound as binding partner for the binding agent which competes binding of said binding agent to the pharmaceutically active form of the parent compound present in the biological sample (if present). If a pharmaceutically active form is not present in the sample, no relevant binding occurs. Said sample may be a biological sample obtained from a patient to be monitored, e.g. from a transplanted patient who has taken AEB071.

According to one embodiment, the concentration of at least one pharmaceutically active form of the parent compound in a sample is determined by comparing the obtained results from the binding assay with a standard calibration curve. A respective standard curve may be obtained by making a calibration curve using a dilution series of the parent compound or an active form thereof. The value obtained for the biological sample may then be compared to the standard curve, thereby allowing the determination of the concentration of the pharmaceutically active form of the parent compound present in the sample.

According to one embodiment, the pharmaceutically active form of the parent compound or the derivative thereof which is recognized by the binding agent is conjugated to a detectable label, and such a conjugate is configured to compete with the pharmaceutically active form of said parent compound present in the sample for binding by the binding agent. Said label provides a signal indicative of a concentration of said pharmaceutically active form of said parent compound in the tested sample when said compound is present in therapeutic drug monitoring concentrations. Examples of respective technologies are for example fluorescence polarization immunoassay (FPIA), cloned enzyme donor immunoassay (CEDIA®), chemiluminescence heterogenous immunoassay (CMIA). Of course, also other homogenous or heterogeneous immunoassays may be used for determining the concentration of the parent compound in this sample. The examples given herein are therefore non-limiting.

According to one embodiment, the target is the derivative that was used for obtaining the binding agent or a variant thereof that is recognized by the binding agent with the same specificity. The target which is used for competing with the pharmaceutically active form of the parent compound in the sample to be analyzed for binding by the binding agent can thus be the derivative that was used for obtaining the respective binding agent. This ensures, that said competing target is bound by the binding agent with the highest specificity. However, it is also possible to use a variant of said derivative, which is recognized by the binding agent preferably with the same specificity. The use of a variant may be feasible if it e.g. facilitates the assay (e.g. by using a different carrier).

According to one embodiment, the binding agent used for performing the competitive assay carries a detectable label. The concentration of the pharmaceutically active form of the parent compound in the sample may then for example be determined by measuring the decrease of the label in the sample, as soon as the sample is added thereto and after appropriate incubation and washing steps were performed.

According to further embodiment, the target which competes with the parent compound for binding by the binding agent is immobilized on a matrix. Said matrix can be of any kind such as for example a chip, a plate comprising multiple wells, a column or any other suitable matrix. For example, the derivatives, which are used for obtaining the binding agent or variants thereof that are still bound and thus recognized by the binding agent may be immobilized on said matrix. The respectively prepared matrix is contacted with the binding agent in the presence of the sample assumed to comprise at least one pharmaceutically active form of the parent compound. Alternatively, the assay may be reversed and the binding agent may be immobilized on the matrix.

Then, binding of said binding agent in the presence of the sample to the derivative/target immobilized on the matrix is detected. For detection, a second binding agent may be added, which recognizes the first binding agent and which carries a detectable label. In case the binding agent is immobilized instead of the derivative/target, the derivative/target is added to the assay and is respectively detected. Detection occurs by detecting said detectable label of said second binding agent.

Therefore, according to one embodiment the drug monitoring assay comprises a binding agent that is labelled and/or wherein a second binding agent is added, that recognises the first binding agent and wherein the second binding agent carries a detectable label.

Detection may occur via an immunoassay. A suitable form for performing a respective immunoassay is an ELISA.

Suitable parent compounds that can be monitored with the drug monitoring assay are described above and may be selected from the group consisting of immunosuppressants, anti-infective agents, antiepileptic drugs, antipsychotics and anticancer drugs.

With a drug monitoring assay according to the present invention also small molecules may be monitored. Suitable small molecules which can be respectively monitored and suitable binding agents for this purpose are described above; we refer to the above disclosure.

According to one embodiment of the present invention, the parent compound to be monitored is the small molecule PKC inhibitor AEB071. For detecting said parent compound in a biological sample, a derivative of AEB071 as generally described above may be used, in particular Derivative A and/or Derivative B. The derivative can be immobilized on a matrix as described herein. The derivatives may comprise a carrier molecule. A respective assay preferably has a working range of 1 to 500, or 1 to 300 ng/ml, or 2 to 250 ng/ml.

Preferably said binding agent, which can be obtained by the methods described above and which is used in the assay of the present invention, is an antibody selected from the group consisting of 2G8, 4G4, 3A3 or 6811.

Also provided with the present invention is a diagnostic kit for determining the concentration of at least one pharmaceutically active form of a parent compound in a sample, comprising at least one binding agent which binds a pharmaceutically active form of the parent compound with a higher specificity than a pharmaceutically inactive form of the parent compound and optionally reagents for determining the concentration of said pharmaceutically active form of said parent compound in said sample.

Suitable binding agents are described above and in the claims. Said diagnostic kit may also comprise a matrix, wherein a target for said binding agent or the binding agent is immobilised on said matrix. A derivative of AEB071 as described above and in the claims or a variant thereof that is recognized by the binding agent with the same specificity can be immobilised on said matrix.

Said binding agent used in the diagnostic kit and/or the competing target may carry a detectable label. However, also a second binding agent may be used which binds said binding agent or the competing target, which carries a detectable label.

Also provided is a matrix, having a derivative as defined in the claims or a binding agent as defined in the claims immobilised thereon. A respective matrix is useful for the described drug monitoring assay.

A label which can be used according to the teachings of the present invention is any molecule that produces, or can be induced to produce, a detectable signal. The label can be conjugated to an analyte, an immunogen, a binding agent, illustratively the binding agent produced by the method described above or a second binding agent having a specificity therefore, or to another molecule such as a receptor or a molecule that can bind to a receptor such as a ligand, particularly a hapten. Non-limiting examples of labels include radioactive isotopes, enzymes, enzyme fragments, enzyme substrates, enzyme inhibitors, coenzymes, catalysts, fluorophores, dyes, chemiluminescencers, luminescers, sensitizers, non-magnetic or magnetic particles, solid supports, liposomes, ligands, receptors and hapten radioactive isotopes.

The term "sample" or "biological sample" refers to a sample assumed to comprise a pharmaceutically active form of the parent compound. It includes, but is not limited to any quantity of a substance from a living thing or formerly living thing. Such living things include, but are not limited to humans, mice, monkeys, rats, rabbits, horses, and other animals. Such substance includes, but is not limited to blood, serum, urine, tears, cells, organs, tissues, bone, bone marrow, lymph, lymph knots, synovial tissue, chondrocytes, synovial macrophages, endothelial cells and skin.

Also provided with the present invention is a diagnostic kit for determining the concentration of at least one pharmaceutically active form of a parent compound in a sample, comprising at least one binding agent which binds a pharmaceutically active form of the parent compound with a higher specificity than a pharmaceutically inactive form of the parent compound for determining the concentration of said pharmaceutically active form of the parent compound in said sample.

The binding agent may be obtained by a method described above. Suitable binding agents are also described in claims 9 to 12. The diagnostic kit may also include appropriate buffers, reagents and instructions for use.

According to one embodiment, the diagnostic kit comprises a matrix, wherein either a target for said binding agent or the binding agent itself is immobilized on said matrix. As described above, a derivative which was used for obtaining the binding agent may be used as target. Alternatively, a variant thereof may be used, that is recognized by the binding agent with the same specificity.

Several suitable methods for detecting the concentration of the parent compound in the biological sample are described above. Depending on the detection method used, the binding agent, the competing target and/or a second binding agent recognizing either the binding agent or the competing target carries a detectable label. The diagnostic kit is particularly useful for monitoring AEB071. Suitable embodiments are described above and can also be used in the diagnostic kit.

Also provided with the present invention is a matrix, either carrying the above described derivatives of AEB071 and particularly Derivative A (BJC) and/or Derivative B (BJC) or a binding agent obtained by the above described screening method. Suitable examples are described above. The derivatives may optionally carry suitable carriers.

EXAMPLES

The present invention is now described in further detail by way of an example, using the generation of appropriate binding agents against AEB071 for establishing a drug monitoring assay.

1. Design of the Derivatives

In order to obtain suitable binding agents, here antibodies which specifically bind an active form of the parent compound AEB071, two derivatives Derivative A (BJC) and Derivative B (BJA) were created (structures see above). These two derivatives are modified AEB071 versions, with activated linkers at two different positions. Both derivatives were chosen for the highest probability to generate antibodies which recognize the parent compound AEB071 and the least probability to recognize pharmacologically inactive metabolites of AEB071. In order to obtain respective antibodies, certain parts of the molecule were shielded by conjugating a KLH carrier protein to the respective site. Said carrier prevents the creation of antibodies against the shielded parts and increase immunogenicity. By using this principle, the specificity of the antibodies can be designed in advance to the potentially decisive sites of the compound where relevant metabolic actions occur by designing the derivatives appropriately. The design of the derivatives determines the available antigen binding sites accessible on the parent compound.

2. Production of Antibodies Specific for the Derivatives

The respective conjugates of the derivatives were used for individual immunizations of rabbits and mice, following standard procedures (see above).

Polyclonal antisera (pAb) were generated in rabbits and tested after individual boosts for reactivity to the derivative conjugates. Final boosts were also subjected to affinity purification on immobilized compounds.

Similarly, monoclonal mouse antibodies (mAb) were generated towards the conjugates. Antibodies were produced from selected cloned hybridoma cell lines. pAb and mAb were generated to both derivatives.

The pAb sera, hybridoma supernatants, as well as purified pAb and mAb were subjected to analysis of specific binding to the antigen, by direct ELISA methods.

3. Selection of AEB071 Specific Antibodies

Those antibodies were selected for further testing that bind specifically at high dilution to the conjugated derivative of the parent compound AEB071 as well as to the parent compound itself. The obtained data shows that the mAb and pAb are highly potent, specific tools for binding assays for those compounds, in particular for using them in drug monitoring assays of AEB071.

During the selection and purification steps, the binding to the parent compound AEB071 was tested. This was done by testing the inhibition of the antibodies binding to the BJC or BJA conjugate by the free drug AEB071. Antibodies were found, respectively selected which displayed a high percentage of inhibition by the free drug AEB071. For the mAb a range of antibodies with different binding, respectively inhibition characteristics were selected for further evaluation.

Inhibition by the free drug AEB071 indicates that the antibodies recognize not only the derivative or its conjugate comprising a carrier, but also the free drug and hence the active parent compound. This is important for developing an AEB071 monitoring assay, in particular an immunoassay, which is specific for the active compound.

Selecting those antibodies, wherein binding was almost completely inhibited by the free drug ensured that most of the antibodies recognized the parent compound rather than the linker or the carrier protein of the derivatives. Therefore, monitoring assays based on competition of binding to differently conjugated or labeled BJC or BJA derivatives by AEB071 are feasible. Suitable examples of respective competitive methods are described above and are also well-known.

The generation of antibodies with different inhibition characteristics allows the selection of antibodies for the development of assays that allow the analysis of a broad range of AEB071 concentrations. Furthermore, raising a variety of respective antibodies also allows selecting those antibodies which may differentiate between the parent compound and different active metabolites.

The direct conjugate binding assays performed, combined with the observed inhibition by the free drug shows feasibility of assays based on the inhibition of the binding of the anti-BJC or anti-BJA antibody by the free drug or closely related compounds in samples from animals or patients, to be quantified versus a calibration curve, based on known concentration of AEB071. The actual concentration of the compound in a sample may be reliably determined this way.

By the selection of AEB071 derivatives together with the performed conjugation strategy and selection strategy for antibodies, valuable assay tools were obtained for the development of new monitoring assays (particularly immunoassays) based on binding of the antibody to the target, which is competed by the compound in question in the sample. Of course, also other competitive assay formats may be used, many of which are known in the prior art.

Specificity Test for Monoclonal and Polyclonal Anti-AEB071 Antibodies

An immunoassay was created, wherein the derivative used for raising the antibodies was fixed to the empty wells of a plate. Afterwards, the selected antibodies were added together with the parent molecule AEB071. After appropriate washing steps, binding of the antibody to the immobilized derivative was detected by using an anti-species PO (peroxidase), antibody and adding the respective substrate OPD (ortho phenyldiamine). The experimental setting was as follows:

A NUNC MaxiSorb 74981 plate was used for fixing the derivative BJA, which carried an egg ovalbumin carrier (ova). This was done by mixing ova-BJA with 1 μg/ml PBS buffer at pH7.4. The mixture was rested over night, at 4° C. The mixture was added to the empty wells of the plate. 200 μl Pierce PBS SuperBlock was added and the respective plates were shaked in the dark, at room temperature for 1 hour. The plates were then washed 3 times with 300 μl washing solution.

The antibodies and the antibodies combined with AEB071 were added to the wells (100 μl) and were incubated for 15 to 30 minutes. The following antibodies were used: Poly antibody (rabbit): anti-BJA and anti-BJC. Mono antibody (mouse): anti-BJA (2G8 and 4G4) and anti-BJC (3A3, 6B11). Incubation was than performed for 2 hours at room temperature, under shaking in the dark. Afterwards, the sample was washed 3 times with 300 μl washing solution. Afterwards, 100 μl of anti-species-PO antibody was added and incubated for 1 hour at room temperature, under shaking in the dark. Afterwards, the samples were washed 3 times with 300 μl wash solution.

Afterwards, the substrate OPD (100 μl) was added. 1 tablet was dissolved in 20 ml distilled water.

Incubation took place for 20 minutes at room temperature in the dark under shaking.

Afterwards, 100 μl Stop solution, $H_2SO_4 2N$ was added.

The OD of the solution was measured at 490 nm.

The following setting was used:

| 1 ug/mL ova-BJA | tested antibodies | AEB071 | anti-species-po antibody | OPD | |
|---|---|---|---|---|---|
| + | + | − | + | + | |
| + | − | − | + | + | |
| − | + | − | + | + | NS1 |
| + | + | + | + | + | |
| + | − | + | + | + | |

The following results were obtained:

| | | +0 ng/mL AEB071 1 2 | +500 ng/mL AEB071 3 4 | +200 ng/mL AEB071 5 6 | +50 ng/mL AEB071 7 8 | No coating NS1 9 10 |
|---|---|---|---|---|---|---|
| pAb anti-BJA | A | 2.028 Coated ova-BJA | 0.993 Coated ova-BJA | 1.166 Coated ova-BJA | 1.034 Coated ova-BJA | 0.071 No coating |

-continued

|  |  | +0 ng/mL AEB071 1 2 | +500 ng/mL AEB071 3 4 | +200 ng/mL AEB071 5 6 | +50 ng/mL AEB071 7 8 | No coating NS1 9 10 |
|---|---|---|---|---|---|---|
| pAb anti- BJC | B | 2.715 Coated ova-BJA | 1.536 Coated ova-BJA | 1.872 Coated ova-BJA | 2.294 Coated ova-BJA | 0.067 No coating |
| 2G8 | C | 1.911 Coated ova-BJA | 0.120 Coated ova-BJA | 0.152 Coated ova-BJA | 0.469 Coated ova-BJA | 0.063 No coating |
| 4G4 | D | 2.628 Coated ova-BJA | 0.076 Coated ova-BJA | 0.089 Coated ova-BJA | 0.270 Coated ova-BJA | 0.065 No coating |
| 3A3 | E | 1.608 Coated ova-BJA | 0.118 Coated ova-BJA | 0.173 Coated ova-BJA | 0.415 Coated ova-BJA | 0.058 No coating |
| 6B11 | F | 2.112 Coated ova-BJA | 0.205 Coated ova-BJA | 0.335 Coated ova-BJA | 0.779 Coated ova-BJA | 0.059 No coating |

The results of the assay are also shown in FIG. 1, wherein inhibition by AEB071 in % OD is indicated (no AEB 071=100% OD). It was found that coating with the small molecule AEB071 is not feasible, as the compound will not properly adhere to the plates (data not shown). However, coating with the original derivative carrying a carrier (for example egg ovalbumin) works. Therefore, a derivative—here ova-BJA—was attached to the plates.

If no coating is used (NS1), no significant signal is obtained. Therefore, the background is low. Also the antispecies conjugated antibodies (B0 and NS2) do not bind unspecifically to the assay. This is also important in order to avoid background.

Binding of all selected antibodies to the immobilized derivative were inhibited when AEB071 was added. This demonstrates, that the used antibodies are all specific for AEB071. The best specificity was obtained with the antibody 4G4.

In order to establish a calibration curve which can be used as a standard to determine the concentration of AEB071 in an unknown sample (for example a biological sample) a dilution series was performed as described by the following table (final concentrations in the well). An inhibition curve of AEB071 against 4G4 and 3A3 in buffer was prepared as follows:

| 1 ug/mL ova-BJA | tested antibodies: 4G4: 1:10'000 2A3: 1:50'000 | AEB071 From 1 to 500 ng/l | anti-species-po antibody | OPD |  |
|---|---|---|---|---|---|
| + | + | + | + | + | Bn |
| + | + | − | + | + | B0 |
| + | − | + | + | + | NS1 |
| + | − | − | + | + | NS2 |
| − | + | − | + | + | NS3 |
|  | − | + | + | + | NS4 |

The final concentrations were as follows in the wells:

| 4G4 1:10'000 | 3A3 1:50'000 | AEB071 in ng/ml buffer |
|---|---|---|
| + | + | 500 |
| + | + | 250 |
| + | + | 125 |
| + | + | 62.5 |
| + | + | 31.2 |
| + | + | 15.6 |
| + | + | 7.8 |
| + | + | 3.9 |
| + | + | 2 |
| + | + | 1 |

Figure 2:
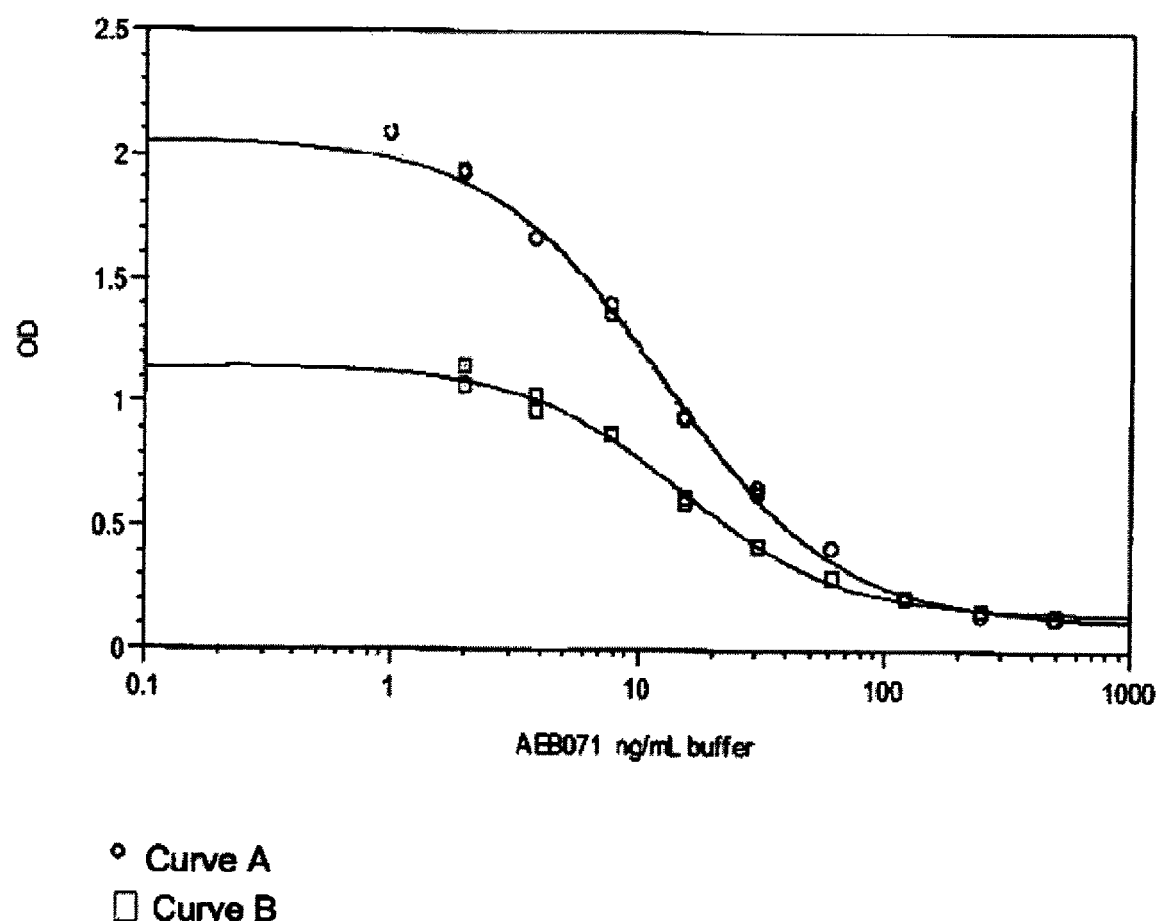
FIG. 2: Calibration curves representative for the results obtained for the antibody 4G4 versus AEB071 (curve A) and antibody 3A3 versus AEB071 (curve B).

By using this dilution series, a calibration curve as described in FIG. 2 was obtained when measuring the OD.

Curve A is representative for the results obtained for the antibody 4G4 versus AEB071.

Curve B is representative for the results obtained for the antibody 3A3 versus AEB071.

The legend to this FIG. 2 reads as follows:

| 4-P Fit: y = $(A - D)/(1 + (x/C)^B) + D$: | A | B | C | D | R°2 |
|---|---|---|---|---|---|
| ○CurveA (curve 4G4@AEB071: Concentration v . . . | 2.058 | 1.218 | 12.998 | 0.108 | 0.997 |
| □CurveB (curve3A3@AEB071: Concentration v . . . | 1.144 | 1.338 | 15.346 | 0.139 | 0.996 |

The results demonstrate that the antibodies obtained with the method of the present invention are suitable for specifically detecting AEB071 in a sample. Antibody 4G4 appears to be even more specific than 3A3 which still showed an acceptable specificity.

The invention claimed is:

1. An antibody that specifically binds the pharmaceutically active form of AEB071 as set forth in formula I:

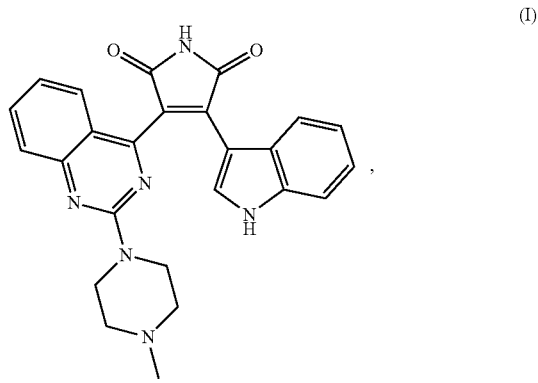

(I)

wherein said antibody also specifically binds a derivative of AEB071 selected from the group consisting of:
(i) BJC, as set forth in formula II
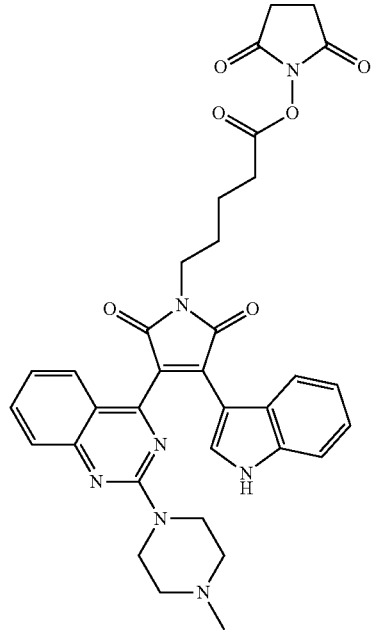
(II)
and
(ii) BJA, as set forth in formula III
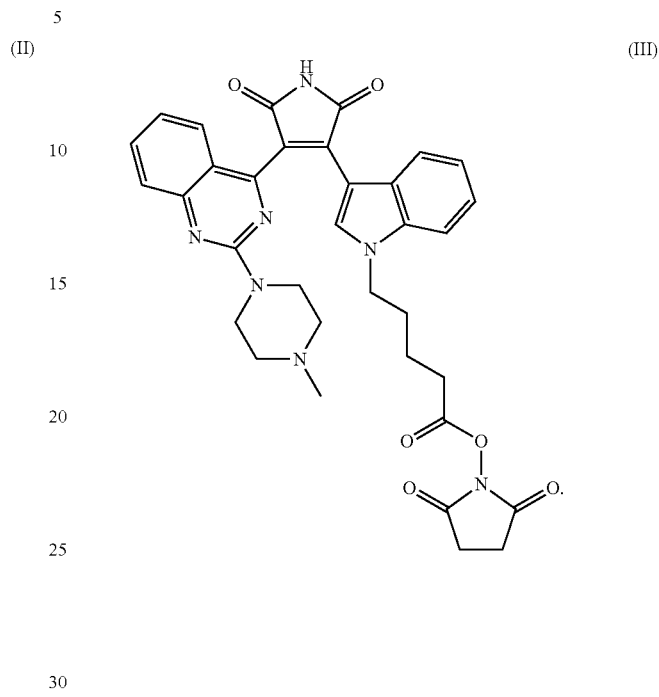
(III)
* * * * *